United States Patent [19]
Bolhofer et al.

[11] 4,415,575
[45] Nov. 15, 1983

[54] SUPPRESSION OF GASTRIC ACID SECRETION USING PYRIMIDYLCARBAMATES

[75] Inventors: William A. Bolhofer, Frederick; John D. Prugh, Chalfont, both of Pa.

[73] Assignee: Merck & Co., Inc., Rahway, N.J.

[21] Appl. No.: 345,957

[22] Filed: Feb. 5, 1982

Related U.S. Application Data

[60] Continuation of Ser. No. 137,061, Apr. 3, 1980, abandoned, which is a division of Ser. No. 20,147, Mar. 13, 1979, Pat. No. 4,226,871.

[51] Int. Cl.$^3$ .............................................. A61K 31/505
[52] U.S. Cl. ................................................... 424/251
[58] Field of Search ......................... 544/332; 424/251

[56]  References Cited

U.S. PATENT DOCUMENTS 4,008,235  2/1977  Lesher et al. ...................... 424/251
4,144,338  3/1979  Bolhofer .............................. 424/251

FOREIGN PATENT DOCUMENTS 1518029  7/1978  United Kingdom .

Primary Examiner—Paul M. Coughlan, Jr.
Attorney, Agent, or Firm—Gabriel Lopez; Salvatore C. Mitri; Hesna J. Pfeiffer

[57]  ABSTRACT

Heterocyclic carbamates are disclosed which have potent gastric secretion inhibitory properties. The heterocyclic substituent is a pyridyl group or a 6-membered heterocycle with two nitrogen heteroatoms, which may be optionally substituted. Further substituents on the carbamate nitrogen and oxygen atoms are also disclosed. The compounds have profound effects on the inhibition of gastric secretions in the gastro-intestinal tract, and compositions for such uses are also disclosed.

2 Claims, No Drawings

SUPPRESSION OF GASTRIC ACID SECRETION USING PYRIMIDYLCARBAMATES

This is a continuation of application Ser. No. 137,061 filed Apr. 3, 1980, now abandoned, which in turn is a division of application Ser. No. 20,147, filed Mar. 13, 1979, now U.S. Pat. No. 4,226,871, issued Oct. 7, 1980.

BACKGROUND OF THE INVENTION

Excess secretion of gastric acid can cause indigestion and stomach distress and, if prolonged, can result in ulcer formation. Treatment of excess secretion of gastric acid has heretofore consisted mainly of a bland diet, abstinence from certain foods and the use of antacids to neutralize the gastric acid after it is secreted into the stomach. An improved method of treatment would result from the inhibition of gastric acid secretion. It is thus an object of the present invention to provide compounds which inhibit gastric acid secretion. Another object is to provide methods for the preparation of these compounds. A further object is to provide pharamaceutical formulations for the administration of these compounds. Still another object to provide a method to inhibit gastric secretion. These and other objects of the present invention will become apparent from the following description.

DESCRIPTION OF THE INVENTION

The compounds of the instant invention are best described by reference to the following structural formula:

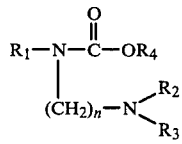
(I)

wherein n is 2 to 4;

$R_1$ is a 6-membered heterocyclic ring with one or two nitrogen heteroatoms which may optionally be substituted with one, two or three of loweralkyl, halogen, trifluoromethyl, loweralkoxy, loweralkylthio, loweralkylsulfonyl or mixtures thereof;

$R_2$ and $R_3$ are loweralkyl; and $R_4$ is loweralkyl or phenyl.

In the instant specification the term "loweralkyl" is intended to include those alkyl groups containing from 1 to 6 carbon atoms in either a straight or branched configuration. Exemplary of such alkyl groups are methyl, ethyl, propyl, isopropyl, butyl, tert-butyl, pentyl, hexyl, and the like.

The term "halogen" is intended to include the halogens of fluoro, chloro, bromo and iodo.

The 6-membered heterocyclic ring with one or two nitrogen heteroatoms include the heterocyclic rings of pyridine, pyrimidine, pyridazine and pyrazine.

PREFERRED EMBODIMENTS OF THE INVENTION

The preferred embodiments of the instant invention are realized in the above structural formula wherein:

n is 2 to 4;

$R_1$ is a 6-membered heterocyclic ring with one or two nitrogen heteroatoms which may optionally be substituted with one or two loweralkyl or halogen;

$R_2$ and $R_3$ are loweralkyl; and $R_4$ is loweralkyl or phenyl.

Other preferred embodiments of the instant invention are realized in the above structural formula wherein $R_1$ is pyridyl or pyrimidinyl optionally substituted with one or two loweralkyl; and n is 2.

Further preferred embodiments are realized when the heterocyclic rings are substituted with one or two methyl groups.

Still further preferred embodiments of this invention are realized in the foregoing fomula wherein the heterocycle is a 2-pyridyl or 2-pyrimidinyl which is substituted with one or two methyl groups;

$R_2$ and $R_3$ are methyl or isopropyl; and $R_4$ is methyl, ethyl or phenyl.

The compounds of the instant invention are prepared by reacting heterocyclic substituted alkylene diamine (III) with an appropriately substituted carbamoyl chloride (IV), according to the following reaction scheme:

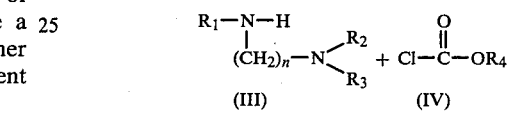
(III) (IV)

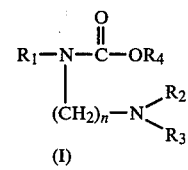
(I)

wherein n, $R_1$, $R_2$, $R_3$ and $R_4$ are as previously defined.

The reaction is carried out by combining the substituted alkylene diamine (III) with the chloroformate (IV) in an inert solvent such as benzene, toluene, tetrahydrofuran, and the like and stirred at from 0° C. to the reflux temperature of the reaction mixture for from 2 hours to 3 days. Since the reaction in its initial period is occasionally exothermic, a useful technique for this process is to have the initial reaction take place at a lower temperature such as from 0° C. to room temperature and then, when the reaction no longer appears exothermic, raise the temperature to the desired reaction temperature.

During the course of the reaction one mole of hydrogen chloride is released for each mole of product produced, and it may be advantageous to include in the reaction mixture a molar equivalent, or a slight excess of a base such as a tertiary amine. The amine reacts with the hydrogen chloride and removes it from possible interference with the reaction.

The compounds of this invention may be isolated and used as the free base or as a pharmaceutically acceptable acid addition salt. Such salts are formed by reaction of the free base with the desired inorganic or organic acid. The salts are prepared using methods known to those skilled in this art. Exemplary inorganic acids are hydrohalic acids such as hydrochloric or hydrobromic, or other mineral acids such a sulfric, nitric, phosphoric and the like. Suitable organic acids are malcic, fumaric, tartaric, citric, acetic, benzoic, succinic, isethionic and the like.

The compounds of the present invention in the described dosages may be administered orally, however, other routes such as intra peritoneal, subcutaneous, intromuscular or intravenous may be employed.

The active compounds of the present invention are orally administered, for example, with an inert diluent or with an assimilable edible carrier, or they may be enclosed in hard or soft gelatin capsules, or they may be compressed into tablets, or they may be incorporated directly with the food of the diet. For oral therapeutic administration, the active compounds of this invention may be incorporated with excipients and used in the form of tablets, troches, capsules, elixirs, suppositories, suspensions, syrups, wafers, chewing gum, and the like. The amount of active compound in such therapeutically useful compositions or preparations is such that a suitable dosage will be obtained.

The tablets, troches, pills, capsules and the like may also contain the following: a binder such as gum tragacanth, acacia, corn starch or gelatin; an excipient such as dicalcium phosphate; a disintegrating agent such as corn starch, potato starch, alginic acid and the like; a lubricant such as magnesium scearate; and a sweetening agent such as sucrose, lactose or saccharin may be added or a flavoring agent such as peppermint, oil of wintergreen, or cherry flavoring. When the dosage unit form is a capsule, it may contain in addition to materials of the above type, a liquid carrier such as a fatty oil. Various other materials may be present as coatings or to otherwise modify the physical form of the dosage unit, for instance, tablets, pills or capsules may be coated with shellac, sugar or both. A syrup or elixir may contain the active compounds, sucrose as a sweetening agent, methyl and propyl parabens as preservatives, a dye and a flavoring such as cherry or orange flavor. Of course, any material used in preparing any dosage unit form should be pharmaceutically pure and substantially non-toxic in the amount employed.

When used in the above formulation, the instant compounds are employed at dosages sufficient to suppress gastric acid secretions. The dosage may be given a single daily dose or in divided dosages throughout the day. The specific dose given to a patient will vary with the severity of the condition, the weight of the patient and the particular compound being employed. As such, dosages of from about 100 to 500 mg. per dose have been found to be effective, administered from 1 to 4 times per day.

EXAMPLE 1

Ethyl N-(2-dimethylaminoethyl)-N-(4,6-dimethyl-2-pyridyl) carbamate Dihydrobromide Into 150 ml. of dry benzene is added 4.3 gm. of triethylamine and 7.5 g. (0.038 mole) of N,N-dimethyl-N'-(4,6-dimethyl-2-pyridyl) ethylene diamine. The mixture is cooled with stirring under nitrogen to 5° C. and 4.67 g. (0.043 mole) of ethyl chloroformate is added and stirred at 5° C. for 4 hours and then at room temperature for 2 days. The reaction mixture is heated at 65°–70° C. for 2 hours, cooled, and 250 ml. of ether is added. The mixture is filtered and the solid washed with ether. The combined ether extracts are concentrated to dryness affording an oil which is dissolved in ether and treated with 48% hydrobromic acid causing the precipitaion of a solid which is filtered and dried. The solid material is recrystallized twice from isopropanol affording 8.0 g. of ehtyl N-(2-dimethylaminoethyl)-N-(4,6-dimethyl-2-pyridyl) carbamate dihydrobromide m.p. 167° C. (with decomposition).

Following the above procedure, using N,N-dimethyl-N'-(4-trifluoromethyl-2-pyridyl) ethylene diamine in place of N,N-dimethyl-n'-(4,6-dimethyl-2-pyridyl) ethylene diamine, there is obtained Ethyl-N-(2-dimethylaminoethyl)-N-(4-trifluoromethyl-2-pyridyl) carbamate dihydromide.

EXAMPLE 2 n-propyl N-(2-dimethylamineothyl)-N-(4,6-dimethyl-2-pyridyl) carbamate Hydrochloride Hemihydrate A solution of 5.80 g. (0.03 mole) of N,N-dimethyl-N'-(4,6-dimethyl-2-pyridyl) ethylene diamine and 4.79 g. (0.045 mole) of n-propyl chloroformate in 50 ml. of dry benzene is heated at reflux for 4 hours and cooled. The formation of a precipitate is observed which is filtered, washed with benzene and dried affording a white powder which is recrystallized from benzene affording 3.61 g. of n-propyl N-(2-dimethylaminoethyl)-N-(4,6-dimethyl-2-pyridyl) carbamate hydrochloride hemihydrate m.p. 99°–102° C. Further recrystallization from butychloride affords product which melts at 100°–102° C.

Following the above procedure, using N,N-dimethyl-N'-(6-methoxy-2-pyridyl) ethylene diamine in place of N,N-dimethyl-N'-(4,6-dimethyl-2-pyridyl) ethylene diamine, there is obtained n-propyl-N-2-dimethylaminoethyl-N-(6-methoxy-2-pyridyl) carbamate hydrochloride.

EXAMPLE 3

Isobutyl N-(2-dimethylaminoethyl)-N-(4,6-dimethyl-2-Pyridyl) carbamate Hydrochloric Hemihydrate Following the procedure of Example 2 using 5.80 g. (0.03 mole) N,N-dimethyl N'(4,6-dimethyl-2-pyridyl) ethylene diamine, and 6.15 g. (0.045 mole) of isobutyl chloroformate in 50 ml. of dry benzene, there is afforded after recrystallization from butyl chloride 3.21 g. of product m.p. 100°–106° C.

EXAMPLE 4 n-Butyl N-(2-dimethylaminoethyl)-N-(4,6-dimethyl-2-pyridyl) carbamate hydrochloride Following the procedure of Example 2 using 5.80 g. (0.03 mole) of N,N-dimethyl-N'-(4,6-dimethyl-2-pyridyl) ethylene diamine, 6.15 g. (0.045 mole) of N-butyl chloroformate in 50 ml. of dry benzene, there is prepared after recrystallization from n-butyl chloride 5.85 g. of n-butyl N-(2-dimethylaminoethyl)-N-(4,6-dimethyl-2-pyridyl) carbamate hydrochloride m.p. 106°–109° C.

EXAMPLE 5

Methyl N-(2-diisopropylaminoethyl)-N-(4,6-dimethyl-2-pyridyl) carbamate 4.99 g. (0.020 mole) of N,N-diisopropyl-N'-(4,6-dimethyl-2-pyridyl) ethylene diamine is placed in 25 ml. of dry tetrahydrofuran and 1.75 ml. (0.022 mole) of methyl chloroformate is added. The reaction mixture is heated at reflux for 3 hours and evaporated to dryness in vacuo affording a white solid. Thin layer chromatographic analysis of the solid material indicates that the reaction is incomplete whereupon 25 ml. of tetrahydrofuran containing 0.9 ml. of methyl chloroformate is added and the mixture heated at reflux for 6 hours. An additional 0.9 ml. of methyl chloroformate is added and the reaction heated at reflux for 5 hours. The reaction is poured into 100 ml. of water and made alkaline and extracted with ether. The ether layer is washed and concentrated affording a tan oil which is chromotographed on 500 g. of silica gel, eluting with 5% methanol in chloroform and collecting 20 ml. fractions. Fractions 13,'340 are collected and evaporated to dryness affording a tan oil. The oil is distilled and the fraction collected at 120°–160° C. at 0.95 nm. of Hg. affording 2.23 g. of methyl N-(2-diisopropylaminoethyl)-N-(4,6-dimethyl-2-pyridyl) carbamate.

Following the above procedure using N,N-dimethyl-N'-(6-methythio-2-pyridyl) ethlene diamine or N,N-dimethyl-N'-(6-methylsulfonyl-2-pyridyl) ethylene diamine in place of N,N-diisopropyl-N'-(4,6-dimethyl-2-pyridyl) ethylene diamine, there is obtained methyl-N-(2-dimethylaminoethyl)-N-(6-methylthio-2-pyridyl) carbamate, and methyl-N-(2-dimethylaminoethyl)-N-(6-methyl sulfonyl-2-pyridyl) carbamate respectively.

EXAMPLE 6

Phenyl N-(5-chloro-2-pyridyl)-N-(2-diisopropylaminoethyl) carbamate Hydrochloride A solution of 12.79 g. (0.05 mole) of N,N-diisopropyl-N'-(5-chloro-2-pyridyl) ethylene diamine in 100 ml. of benzene is combined with 7.83 g. (0.05 mole) of phenyl chloroformate in 50 ml. benzene over 1 hour at room temperature. The reaction mixture is filtered and the solid material washed 3 times with benzene and dried affording a white powder. The solid material is recrystallized from isopropanol affording 1.53 g. of phenyl N-(5-chloro-2-pyridyl)-N-(2-diisopropylaminoethyl) carbamate hydrochloride m.p. 209°–211° C.

Following the above procedure using N,N-diisopropyl-N'-(4-trifluoromethyl-6-methyl-2-pyridyl) ethylene diamine or N,N-diisopropyl-N'-(4-methyl-6-chloro-2-pyridyl)-ethylene diamine in place of N,N-diisopropyl-N'-(5-chloro-2-pyridyl) ethylene diamine, there is obtained phenyl N-(2-diisopropylaminoethyl)-N-(4-trifluoromethyl-6-methyl-2-pyridyl) carbamate hydrochloride or phenyl N-(2-diisopropylaminoethyl)-N-(4-methyl-6-chloro-2-pyridyl) carbamate hydrochloride respectively.

EXAMPLE 7

Ethyl N-(2-diisopropylaminoethyl)-N-(4,6-dimethyl-2-pyrimidinyl) carbamate Hydrochloride To a solution of 7.51 g. (0.03 mole) of N,N-diisopropyl) N'(4,6-dimethyl-2-pyrimidinyl) ethylene diamine in 50 ml. of tetrahydrofuran is added a solution of 3.14 ml. (0.03 mole) of ethyl chloroformate in 50 ml. of tetrahydrofuran. The reaction mixture is heated at reflux for 3 hours. A thin layer chromatographic analysis of the reaction mixture indicates the reaction is incomplete thus an additional 1.5 ml. of ethyl chloroformate is added and the reaction mixture heated at reflux for 6 hours. The mixture is poured onto 200 ml. of water and made alkaline with sodium hydroxide. The mixture is extracted 3 times with ether and the ether layers washed twice with water and once with saturated sodium chloride solution. The ether layer is dried over magnesium sulfate and evaporated to dryness in vacuo affording a white solid. The crude product is taken up in 30 ml. of warm ethanol and the solution treated with 5 ml. of 5.7 molar ethanolic hydrochloric acid. The solution is diluted with 80 ml. of ether to induce crystallization. The solid material is filtered affording 2.9 g. of ethyl N-(2-diisopropylaminoethyl)-N-(4,6-dimethyl-2-pyrimidinyl) carbamate hydrochloride m.p. 152°–156° C.

EXAMPLE 8

Phenyl N-(2-dimethylaminoethyl)-N-(4,6-dimethyl-2-pyridyl) Carbamate

Over a period of 15 minutes, 7.85 g. (0.05 mole) of phenylchloroformate in added dropwise to a well stirred solution of 9.6 g. (0.05 mole) of N,N-dimethyl-N'-(4,6-dimethyl-2-pyridyl) ethylene diamino in 60 ml. of tetrahydrofuran, containing 5.2 g. (0.05 mole) of triethylamine maintaining the reaction vessel in an ice bath. A white solid begins to separate from the reaction mixture. The reaction mixture is stirred at room temperature for 24 hours. The suspension is filtered and the filtrate evaporated to dryness in vacuo to give 15 g. of a pale tan solid residue which is taken up in about 500 ml. of ether, and filtered. The ether is evaporated to a volume of about 200 ml. and cooled. The ether layer is decanted from 7.8 g. of solid material and the ether layer evaporated to about 50 ml. and cooled affording a second crop of 3.6 g. The filtrate is diluted with 150 ml. of petroleum ether and evaporated to a volume of about 100 ml. affording a third crop of 0.7 g. The three crops of materials are combined and taken up in 500 ml. of hexane, filtered, evaporated to about 300 ml. and cooled to room temperature affording 10.5 g. of phenyl N(2-dimethylaminoethyl)-N-(4,6-dimethyl-2-pyridyl) carbamate, m.p. 109°–112° C.

What is claimed is:

1. A method for the suppression of gastric acid secretions which comprises administering to an animal with excess gastric acid secretions an effective amount of a compound having the formula:

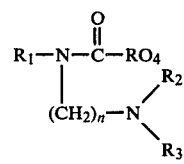

Wherein
n is 2 to 4;
$R_1$ is pyrimidyl, which may optionally be substituted with one, two or three of loweralkyl, halogen, trifluoromethyl, loweralkoxy, loweralkylthio, loweralkylsulfonyl or mixtures thereof;
$R_2$ and $R_3$ are loweralkyl; and
$R_4$ is loweralkyl or phenyl and the pharmaceutically acceptable acid addition salts thereof.

2. A composition for the suppression of gastric acid secretions which comprises a pharmaceutically inert carrier and an effective amount of a compound having the formula

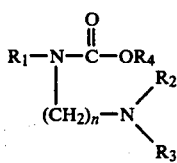
wherein
n is 2 to 4;
R₁ is pyrimidyl, which may optionally be substituted with one, two or three of loweralkyl, halogen, trifluoromethyl, loweralkoxy, loweralkylthio, loweralkysulfonyl or mixtures thereof;
R₂ and R₃ are loweralkyl; and
R₄ is loweralkyl or phenyl and the pharmaceutically acceptable acid addition salts thereof.
* * * * *